US012751684B2

(12) United States Patent
Schweikert et al.

(10) Patent No.: US 12,751,684 B2
(45) Date of Patent: Oct. 6, 2026

(54) PROVIDING ADJUSTED RECORDING PARAMETERS

(71) Applicant: Siemens Healthineers AG, Forchheim (DE)

(72) Inventors: Benjamin Schweikert, Gutenstetten (DE); Bjoern Kreisler, Hausen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 142 days.

(21) Appl. No.: 18/928,881

(22) Filed: Oct. 28, 2024

(65) Prior Publication Data

US 2025/0134485 A1 May 1, 2025

(30) Foreign Application Priority Data

Oct. 31, 2023 (DE) ..................... 10 2023 210 809.7

(51) Int. Cl.
*A61B 6/00* (2024.01)
*A61B 6/42* (2024.01)
*G01T 1/17* (2006.01)

(52) U.S. Cl.
CPC ............ *A61B 6/542* (2013.01); *A61B 6/4241* (2013.01); *A61B 6/5205* (2013.01); *G01T 1/17* (2013.01)

(58) Field of Classification Search
None
See application file for complete search history.

(56) References Cited

U.S. PATENT DOCUMENTS

| | | | | |
|---|---|---|---|---|
| 11,076,823 | B2 * | 8/2021 | Tamura | A61B 6/035 |
| 2015/0199478 | A1 | 7/2015 | Bhatia et al. | |
| 2018/0018757 | A1 * | 1/2018 | Suzuki | G06T 3/4053 |
| 2018/0038969 | A1 * | 2/2018 | McCollough | A61B 6/545 |
| 2019/0099148 | A1 * | 4/2019 | Rupcich | H05G 1/265 |
| 2019/0150864 | A1 | 5/2019 | Flohr et al. | |
| 2020/0388058 | A1 * | 12/2020 | Zhang | G06T 12/10 |
| 2021/0019882 | A1 * | 1/2021 | Hofmann | A61B 6/032 |
| 2022/0130520 | A1 * | 4/2022 | Xia | G16H 50/30 |
| 2024/0169531 | A1 * | 5/2024 | Matsuura | G06T 7/0012 |

FOREIGN PATENT DOCUMENTS

| | | | |
|---|---|---|---|
| CN | 116725567 | A | 9/2023 |
| DE | 102021203273 | A1 | 10/2022 |

* cited by examiner

*Primary Examiner* — Marcus H Taningco
(74) *Attorney, Agent, or Firm* — Harness, Dickey & Pierce, P.L.C.

(57) ABSTRACT

A computer-implemented method comprises: capturing spatially resolved dose profiles for an x-ray imaging scan of at least one examination object in accordance with initial recording parameters via a photon-counting x-ray detector, wherein each photon-counting detector element provides a dose value depending on a number of detected x-ray photons after an interaction between x-ray radiation and the at least one examination object, and wherein the dose profiles are formed by the dose values of the detector elements of each of one or more x-ray imaging scans; and provisioning adjusted recording parameters by applying a trained function to input data, wherein the input data is based on the initial recording parameters and the dose profiles, and the trained function is based on a dose-aware signal quality metric.

20 Claims, 7 Drawing Sheets

PROVIDING ADJUSTED RECORDING PARAMETERS

CROSS-REFERENCE TO RELATED APPLICATION(S)

The present application claims priority under 35 U.S.C. § 119 to German Patent Application No. 10 2023 210 809.7, filed Oct. 31, 2023, the entire contents of which is incorporated herein by reference.

FIELD

One or more embodiments of the present invention relate to a computer-implemented method for providing adjusted recording parameters, to a computer-implemented method for providing a trained function, to a provision unit, to a medical x-ray device, to a training device and to a non-transitory computer program product.

BACKGROUND

Computed tomography systems (CT systems) usually have at least one recording arrangement able to be rotated about an examination object, with an x-ray source and an x-ray detector. The recording arrangement with the x-ray source and the x-ray detector is thus part of a rotatable element of the CT system, which can be guided for example in a gantry of the CT system, which is part of a fixed element. In order to be able to determine CT image datasets of the examination object, after x-ray imaging of the examination object with the at least one x-ray detector, detected measurement data is acquired. From the measurement data a CT image dataset can be reconstructed, for example a set of sectional images and/or a three-dimensional image volume.

In CT systems or in x-ray facilities generally the requirement exists for the x-rays applied to have to be able to be translated in each case into an x-ray image capable of diagnosis. The image quality of the x-ray images is proportional to the x-ray dose applied. The disadvantage is that frequently an unnecessarily large x-ray dose is applied for an x-ray examination in order to be able to obtain a desired image quality for a corresponding diagnosis.

Dose values, for example a Computed Tomography Dose Index (CDTI) of different CT systems, especially for CT systems of different sites, can be compared and their minimum and maximum of the x-ray dose can be determined. This enables sites to be informed about values that are too high and said values to be optimized, for example by training the operating personnel. Reference sites with lower x-ray doses and good image quality can form the basis for the optimization for example. This procedure however is often expensive and possibly susceptible to errors.

SUMMARY

An object of one or more example embodiments of the present invention is to make possible an x-ray imaging scan of an examination object with efficient doses.

At least this object is achieved in accordance with embodiments of the present invention as captured in the independent claims. Advantageous forms of embodiments with expedient developments are the subject matter of the dependent claims.

Independent of the grammatical term usage, individuals with male, female or other gender identities are included within the term.

An inventive way in which the object is achieved with regard to both the methods and apparatuses for providing adjusted recording parameters and also with regard to methods and apparatuses for providing a trained function is described below. Features, advantages and alternate forms of embodiment of data structures and/or functions for methods and apparatuses for providing adjusted recording parameters can be transferred by analogy to data structures and/or functions for methods and apparatuses for providing a trained function. Similar data structures can be in particular identified here by the use of the prefix "training". Furthermore the trained functions used in methods and apparatuses for providing adjusted recording parameters can in particular have been adjusted and/or provided by methods and apparatuses for providing a trained function.

In a first aspect, an embodiment of the present invention relates to a computer-implemented method for providing adjusted recording parameters. In a first step spatially resolved dose profiles for an x-ray imaging scan of at least one examination object in each case are acquired by initial recording parameters via a photon-counting x-ray detector. In this case the x-ray detector has a number of photon-counting detector elements, which each provide a dose value as a function of a number of detected x-ray photons after an interaction of the x-ray radiation with the at least one examination object. The dose profiles are further formed by the dose values of the detector elements of one of the number of x-ray imaging scans in each case. In a further step the adjusted recording parameters are provided by applying a trained function to input data. In such cases the input data is based on the initial recording parameters and the dose profiles. Moreover the trained function is based on a dose-aware signal quality metric. The adjusted recording parameters can further be provided as output data of the trained function.

The steps of the proposed method described here can be partly or completely computer-implemented. Moreover the steps of the proposed method can be carried out, at least in part, in particular completely, after one another or at least partly simultaneously.

The examination object can for example be a human and/or animal male or female patient and/or an examination phantom.

The acquisition of the spatially resolved dose profiles can comprise a receipt and/or acceptance of the dose profiles. The receipt of the dose profiles can in particular comprise an acquisition and/or reading out of a computer-readable data memory and/or a receipt from a data storage unit, for example a database. The dose profiles can further be provided by a provision unit of a medical X-ray device.

The initial recording parameters can refer to recording parameters already predetermined before the beginning of the method. In this case the initial recording parameters can for example be received, in particular acquired and/or read out, from a computer-readable data memory and/or received from a data memory unit, for example a database. As an alternative or in addition the initial recording parameters can be acquired and predetermined by a user input of medical personnel, for example via an input unit. The initial recording parameters can comprise instructions, specifications, commands and/or operating parameters, which cause a medical x-ray device to carry out an x-ray imaging scan of the examination object.

The x-ray device can comprise an x-ray source and the photon-counting x-ray detector. In this case the x-ray source and the x-ray detector can be arranged in a defined arrangement opposite one another, for example on a C-arm, an O-arm or a gantry. The x-ray imaging scan of the examination object can comprise sending out x-ray radiation via the x-ray source in accordance with the initial recording parameters for imaging the examination object arranged between the x-ray source and the x-ray detector.

The x-ray detector has a number of photon-counting detector elements, which can be arranged in rows, columns and/or in the shape of a grid. The detector elements can each be embodied for counting x-ray photons that were emitted by the x-ray source during the x-ray imaging scan. To this end the detector elements can each have a number of pixels, wherein the x-ray photons arriving at the pixels can be counted. For each pixel in such cases different energies, for example four different energies, of x-ray photons can be distinguished by each of the detector elements. The distinction of the energies, in particular of the photon energies, can be undertaken for example by assigning the energies of the detected x-ray photons to four intervals. For example four different energy levels can be distinguished per detector element, i.e. the x-ray photons falling in each case into the energy intervals produced thereby can be counted separately.

To this end the detector elements can each receive physical signals, for example x-ray photons, wherein corresponding data for example describes the x-ray photons counted per pixel of the detector element and/or the x-ray photons counted in each case for various energy intervals. The data recorded by the detector elements can be transferred to an electrical circuit or read out by said circuit from the detector elements. In order to undertake further processing of the data recorded by the detector elements, the electrical circuit can comprise a memory facility with at least one memory block. The data created by the detector elements can be stored at least temporarily in the memory block. The individual detector elements can preferably be designed as Application Specific Integrated Circuits (ASIC). With the aid of the x-ray photons counted over a predetermined acquisition time via the detector elements, a dose value is determined for each detector element, in particular a dose value for each pixel.

Conventional, in particular integrating, x-ray detectors have as their operating principle a noise-prone integration of the detected signals over time. By using a photon-counting x-ray detector statistical information about signal per voxel can be captured much more precisely.

In this case the dose profiles are formed by the dose values of the detector elements, in particular the dose values of all detector elements of one of the number of x-ray imaging scans in each case. The dose profiles can map the dose values of the number of x-ray imaging scans in a spatially resolved manner two-dimensionally (2D) or three-dimensionally (3D).

The trained function maps input data to output data. Here the output data in particular can furthermore depend on one or more parameters of the trained function. The one or more parameters of the trained function can be determined and/or adjusted by a training. The determination and/or the adjustment of the one or more parameters of the trained function can in particular be based on a pair of training input data and associated training output data, in particular comparison output data, wherein the trained function is applied for the creation of training mapping data to the training input data. In particular the determination and/or the adjustment can be based on a comparison of the training mapping data and the training output data, in particular comparison output data. In general a trainable function, i.e. a function with one or more not yet adjusted parameters, is also designated as a trained function.

Other terms for trained functions are trained mapping specification, mapping specification with trained parameters, function with trained parameters, machine learning algorithm. An example of a trained function is an artificial neural network, wherein edge weights of the artificial neural network correspond to the parameters of the trained function. Instead of the term "neural network" the term "neural net" can also be used. In particular a trained function can also be a deep neuronal network, deep artificial neural network. A further example of a trained function is a Support Vector Machine, furthermore in particular other machine learning algorithms are also able to be employed as a trained function.

The trained function can in particular be trained via a back propagation. First of all training imaging data can be determined by application of the trained function to the training input data. After this a deviation between the training imaging data and the training output data, in particular the comparison output data, can be established by application of an error function to the training imaging data and the training output data, in particular the comparison output data. Further, at least one parameter, in particular a weighting of the trained function, can be adjusted iteratively. This enables the deviation between the training imaging data and the training output data, in particular the comparison output data, to be minimized during the training of the trained function.

Advantageously the trained function, in particular the neural network, has an input layer and an output layer. In this case the input layer can further be embodied for receipt of input data. The output layer can be embodied for provision of imaging data, in particular the output data. In such cases the input layer and/or the output layer can each comprise a number of channels, in particular neurons.

The input data of the trained function is based on the initial recording parameters. In particular the input data of the trained function comprises the initial recording parameters. The trained function further provides the adjusted recording parameters as output data. The trained function is based on a dose-aware signal quality metric. In this case at least one parameter of the trained function can be adjusted based on a comparison between adjusted training recording parameters and adjusted comparison recording parameters. In particular the trained function can be provided by a form of embodiment of the proposed method for provision of a trained function, which is described in the further course of this document.

The adjusted recording parameters can have all features and characteristics of the initial recording parameters. The trained function provides the adjusted recording parameters as output data. Advantageously the trained function can provide an adjusted recording parameter in each case for each of the initial recording parameters. The adjusted recording parameters and the initial recording parameters can differ for example by one or more parameter values.

The provision of the adjusted recording parameters can comprise storage on a computer-readable memory medium and/or display on a display unit and/or transmission to a provision unit. The adjusted recording parameters can thus make possible a retrospective optimization of scan protocols in respect of x-ray dose and signal-to-noise ratio (SNR). As an alternative or in addition the adjusted recording parameters can be used for optimization of the scan protocols during the x-ray imaging scan as "real-time" dose modulation from one rotation run to the next rotation run.

In a further advantageous form of embodiment of the proposed method for provision of adjusted recording parameters the input data of the trained function can be based in each case on a minimum value and/or maximum value and/or average value of the dose profile.

Advantageously, for each of the dose profiles, a minimum value, in particular a minimum dose value, and/or a maximum value, in particular a maximum dose value, and/or an average value, in particular a, for example weighted, average value of the dose values, can be determined. In this case the input data of the trained function can be based, in particular exclusively or additionally, on the minimum values and/or maximum values and/or average values of the dose profiles. In particular the input data of the trained function can comprise a minimum value and/or maximum value and/or average value for the dose profiles in each case.

The minimum values, maximum values and/or average values of the dose profiles can represent a measure of how much x-ray radiation, after the examination object, has still reached the x-ray detector at least, maximally or in the middle. A certain amount of x-ray quantas can be needed per voxel in order to reach a sufficient SNR for a diagnostic image quality. X-ray radiation exceeding this can represent an unnecessary dose load for the examination object. Advantageously the present form of embodiment can make possible an improved adjustment of the recording parameters for minimization of the x-ray dose while at the same time maintaining the image quality necessary for diagnostic purposes.

In a further advantageous form of embodiment of the proposed method for provision of adjusted recording parameters the initial recording parameters can have information about a region of the at least one examination object to be imaged and/or a recording trajectory and/or a recording sequence and/or an operating parameter for operating the x-ray source and/or the x-ray detector.

The initial recording parameters can advantageously have information, for example room coordinates and/or geometry parameters, for a region to be imaged (field-of-view) via the x-ray imaging scan, in particular a 2D or 3D region, of the at least one examination object, for example a spatial position and/or alignment and/or shape and/or extent of the region to be imaged. As an alternative or in addition the initial recording parameters can have information about a recording trajectory, for example a 2D or 3D path. In this case the recording trajectory can predetermine a number of positionings for the x-ray source and/or the x-ray detector, in particular with regard to the at least one examination object, for carrying out the x-ray imaging scan. As an alternative or in addition the initial recording parameters can comprise a recording sequence, in particular a temporal and/or spatial sequence of recording positionings of the x-ray source and the x-ray detector and/or a temporal sequence of operating parameters for operation of the x-ray source and/or of the x-ray detector. As an alternative or in addition the initial recording parameters can have an operating parameter, for example a tube voltage of the x-ray source and/or a detection rate of the x-ray detector, for operation of the x-ray source and/or of the x-ray detector, in particular for the x-ray imaging scan of the at least one examination object.

Advantageously the adjusted recording parameters, in particular similarly to the initial recording parameters, can have information about an adjusted region to be imaged of the at least one examination object and/or an adjusted recording trajectory and/or an adjusted recording sequence and/or an adjusted operating parameter for operation of the x-ray source and/or of the x-ray detector.

Advantageously the adjusted recording parameters can be provided for a further x-ray imaging scan via the x-ray source and the x-ray detector. The adjusted recording parameters in this case can make possible an adjusted control of the x-ray source and of the x-ray detector for an x-ray imaging scan of the at least one examination object or of a further examination object.

In a further advantageous form of embodiment of the proposed method for provision of adjusted recording parameters the initial recording parameters can comprise at least one initial reconstruction parameter for reconstruction of image data from the dose values.

The initial recording parameters can advantageously comprise at least one initial reconstruction parameter, in particular a number of initial reconstruction parameters, for reconstruction of image data from the dose values.

The at least one initial reconstruction parameter can advantageously comprise a specification for reconstruction of the image data from the dose values, in particular a 2D or 3D image of the examination object for one or more of the x-ray imaging scans in each case. The reconstruction can for example comprise an, in particular filtered, backprojection of the image data from the dose values, for example.

The initial reconstruction parameters can for example define an imaging geometry and/or slice thickness and/or voxel size. For example the initial reconstruction parameters can be identified with the aid of an, in particular manual or automatic, empirical preselection of reconstruction parameters.

In this case the input data of the trained function can advantageously be based on the at least one initial reconstruction parameter, in particular comprise the at least one initial reconstruction parameter.

The proposed form of embodiment can advantageously make possible an adjustment of the recording parameters while additionally taking into account a later reconstruction of image data from the measurement data to be recorded of the x-ray imaging scan. In particular this enables a low-noise representation of small voxels with very low dose values to be improved, with said voxels having a small slice thickness and a high spatial resolution within the slice plane.

In a further advantageous form of embodiment of the proposed method for provision of adjusted recording parameters the adjusted recording parameters can comprise at least one adjusted reconstruction parameter.

Advantageously the adjusted recording parameters, in particular similarly to the initial recording parameters, comprise at least one adjusted reconstruction parameter, in particular a number of adjusted reconstruction parameters. The at least one adjusted reconstruction parameter can in particular have all features and characteristics that have been described with regard to the at least one initial reconstruction parameter and vice versa. In particular the output data of the trained function can comprise the at least one adjusted reconstruction parameter.

The proposed form of embodiment can advantageously make possible an adjustment of the recording parameters including at least one reconstruction parameter. This advantageously enables an adjustment of the reconstruction of the image data from the measurement data to be recorded via the adjusted recording parameters.

In a second aspect, an embodiment of the present invention relates to a computer-implemented method for provision of a trained function. In a first step spatially resolved training dose profiles for a real or simulated x-ray imaging scan of at least one training examination object are acquired in accordance with various initial training recording parameters via a photon-counting x-ray detector. In this case the x-ray detector has a number of photon-counting detector elements, which each provide a training dose value as a function of a number of detected x-ray photons after an interaction of the x-ray radiation with the at least one training examination object. Moreover, the training dose profiles are each formed by the training dose values of the detector elements of one of a number of x-ray imaging scans in each case. In a further step a first classification of the training dose profiles takes place based on the respective initial training recording parameters. In a further step a second classification of the classified training dose profiles into conforming and deviating training dose profiles takes place by application of a dose-aware signal quality metric, which evaluates the signal quality while taking into account a respective overall dose, to the training dose profiles within a first class in each case. In a further step adjusted comparison recording parameters based on the initial training recording parameters of the training dose profiles classified as conformant are provided. In a further step adjusted training recording parameters are provided by application of the trained function to input data. In this step the input data is based on the initial training recording parameters and the training dose profiles. In a further step at least one parameter of the trained function is adjusted based on a comparison between the adjusted training recording parameters and the adjusted comparison recording parameters. In a further step the trained function is provided.

The steps of the proposed method described above can be carried out at least in part, in particular completely, after one another or at least partly at the same time.

The at least one training examination object can for example be a human and/or animal male or female patient and/or an examination phantom.

The acquisition of the spatially resolved training dose profiles can comprise a receipt and/or recording of the training dose profiles. The receipt of the training dose profiles can in particular comprise an acquisition and/or reading out of a computer-readable data memory and/or a receipt from a data memory unit, for example a database. The training dose profiles can further be provided by a provision unit of a medical X-ray device. The training dose profiles can in particular have all features and characteristics of the dose profiles that have been described with regard to the method for the provision of adjusted recording parameters, and vice versa.

The training dose profiles can be formed by training dose values of detector elements, in particular by training dose values of all detector elements of each or of a number of real x-ray imaging scans. As an alternative the training dose values can be determined by simulation of a number of x-ray imaging scans in accordance with the various initial training recording parameters. In this case the training dose profiles can be formed by the training dose values of one of the number of simulated x-ray imaging scans in each case. The training dose profiles can map the training dose values of the number of real or simulated x-ray imaging scans in a spatially resolved manner in two or three dimensions.

Advantageously in the first classification the training dose profiles are classified based on the respective initial training recording parameters. The initial training recording parameters can advantageously have all features and characteristics of the initial recording parameters that have been described with regard to the method for provision of adjusted recording parameters and vice versa. The initial training recording parameters can designate training recording parameters predetermined before the beginning of the method. In this case the initial training recording parameters can be received for example, in particular acquired and/or read out, from a computer-readable data memory and/or received from a data memory unit, for example a database. As an alternative or in addition the initial training recording parameters can be acquired and predetermined by a user input of a medical operator, for example via an input unit. The initial training recording parameters can comprise instructions, specifications, commands and/or operating parameters, which cause a medical x-ray device to carry out an x-ray imaging scan of the examination object.

The initial training recording parameters can in this case predetermine a kind of recording and/or a region to be imaged of the training examination object. The training dose profiles can be classified in the first classification according to the specification based on the initial training recording parameters. The first classification can in this case in particular be based on a match between individual or a number of initial training recording parameters of a number of training dose profiles. In this case the first classification can comprise a first distinction and/or grouping of the training dose profiles based on the respective initial training recording parameters, for example via a comparison of a pair of training dose profiles based on the respective initial training recording parameters.

Furthermore the training dose profiles classified in accordance with the first classification can be classified in a second classification into conformant and deviating training dose profiles by application of the dose-aware signal quality metric. The dose-aware signal quality metric can advantageously be embodied to evaluate a signal quality, for example an SNR and/or a contrast-to-noise ratio (CNR), while taking into account the x-ray dose applied during the x-ray imaging scan, for example as a boundary condition. For example the dose-aware signal quality metric can assign a quality value to each of the training dose profiles, which evaluates the signal quality of the training dose profile while taking into account the x-ray dose that would be necessary for this recording.

For the second classification a comparison value can be predetermined or determined. The second classification can in this case be a subclassification of the first classification. Advantageously, for each of the first classifications in each case a comparison value or a global comparison value is predetermined or determined. When a comparison value is predetermined, the comparison value can be defined for example with the aid of a user input. As an alternative the comparison value can be determined with the aid of the quality values of the training dose profiles, for example as an average value of the quality values. In particular the comparison value can be determined as the average value of the quality values of a number of different sites.

In the second classification of the classified training dose profiles the classified training dose profiles can be classified in accordance with a deviation of their respective quality value from the comparison value as a conformant or deviating training dose profile. For example, the classified training dose profiles of which the quality value has a deviation within a predetermined standard deviation as regards the comparison value are classified as conformant training dose profiles and the other training dose profiles as deviating training dose profiles. Thus the second classification comprises a comparison between the classified training dose profiles and the global comparison value or the respective comparison value of the corresponding first class.

The adjusted comparison recording parameters can be provided based on the initial training recording parameters of the training dose profiles classified as conformant. In this case adjusted comparison recording parameters can be provided in each case for each of the first classes of the training dose profiles. The adjusted comparison recording parameters can be provided for example as the initial training recording parameters of the training dose profile with the highest quality value in each case per first class. As an alternative the adjusted comparison recording parameters can be provided as an average value of the initial training recording parameters of the training dose profiles classified within a respective first class as conformant.

Advantageously the adjusted training recording parameters can be provided by the application of the trained function to the input data. In this case the input data of the trained function can be based on the initial training recording parameters and the training dose profiles, in particular comprises the initial training recording parameters and the training dose profiles. The trained function can provide the adjusted training recording parameters as output data.

The comparison of the adjusted training recording parameters with the adjusted comparison recording parameters enables the at least one parameter of the trained function to be adjusted. The comparison can comprise a determination of a deviation between the adjusted training recording parameters and the adjusted comparison recording parameters. In this case the at least one parameter of the trained function can advantageously be adjusted in such a way that deviation is minimized. The adjustment of the at least one parameter of the trained function can comprise an optimization, in particular a minimization of a cost value of a cost function, wherein the cost function characterizes the deviation between the adjusted training recording parameters and the adjusted comparison recording parameters, in particular quantifies it. In particular the adjustment of the at least one parameter of the trained function comprises a regression of the cost value of the trained function.

The provision of the trained function can in particular comprise storage on a computer-readable memory medium and/or transmission to a provision unit.

Advantageously, with the proposed method, a trained function can be provided which can be used in one form of embodiment of the method for provision of adjusted recording parameters.

In a further advantageous form of embodiment of the proposed method for provision of a trained function the input data of the trained function can be based on a minimum value and/or maximum value and/or average value of the training dose profiles.

Advantageously a minimum value, in particular a minimum training dose value, and/or a maximum value, in particular a maximum dose value, and/or an average value, in particular a, for example weighted, average value of the training dose values can be determined for the training dose profiles in each case. In this case the input data of the trained function can be based, in particular exclusively or additionally, on the minimum values and/or maximum values and/or average values of the training dose profiles. In particular the input data of the trained function comprises a minimum value and/or maximum value and/or average value for the training dose profiles in each case.

In a further advantageous form of embodiment of the proposed method for provision of a trained function the initial training recording parameters can have information for a region to be imaged of the at least one examination object and/or of a recording trajectory and/or of a recording sequence and/or an operating parameter for operation of the x-ray source and/or of the x-ray detector.

The initial training recording parameters can advantageously have information, for example room coordinates and/or geometry parameters, for a imaging scan region to be imaged (FOV) via the x-ray, in particular a 2D or 3D region, of the at least one training examination object, for example a spatial position and/or alignment and/or shape and/or extent of the region to be imaged. As an alternative or in addition the initial training recording parameters can have information about a recording trajectory, for example a 2D or 3D path. In this case the recording trajectory can predetermine a number of positionings for the x-ray source and/or the x-ray detector, in particular with regard to the at least one training examination object, for carrying out the x-ray imaging scan. As an alternative or in addition the initial training recording parameters can comprise a recording sequence, in particular a temporal and/or spatial sequence of recording positionings of the x-ray source and of the x-ray detector and/or a temporal sequence of operating parameters for operation of the x-ray source and/or of the x-ray detector. As an alternative or in addition the initial training recording parameters have an operating parameter, for example a tube voltage of the x-ray source and/or a detection rate of the x-ray detector, for operation of the x-ray source and/or of the x-ray detector, in particular for the x-ray imaging scan of the at least one training examination object.

Advantageously the adjusted comparison recording parameters, in particular similarly to the initial training recording parameters, can have information about an adjusted region to be imaged of the at least one examination object and/or of an adjusted recording trajectory and/or of an adjusted recording sequence and/or an adjusted operating parameter for operation of the x-ray source and/or of the x-ray detector.

In a further advantageous form of embodiment of the proposed method for provision of a trained function the initial training recording parameters can comprise at least one initial training reconstruction parameter for reconstruction of image data from the training dose values.

The initial training recording parameters can advantageously comprise at least one initial training reconstruction parameter, in particular a number of initial training reconstruction parameters, for reconstruction of image data from the training dose values. The at least one initial training reconstruction parameter can in particular have all features and characteristics of the at least one initial reconstruction parameter that have been described with regard to the method for provision of adjusted recording parameters and vice versa.

The at least one training reconstruction parameter can advantageously comprise a specification for reconstruction of the image data from the training dose values, in particular a 2D or 3D mapping of the at least one training examination object from one or a number of x-ray imaging scans in each case. The reconstruction can for example comprise an in particular filtered backprojection of the image data from the training dose values.

In this case the input data of the trained function can advantageously be based on the at least one initial training reconstruction parameter, in particular comprises the at least one initial training reconstruction parameter.

In a further advantageous form of embodiment of the proposed method for provision of a trained function the adjusted comparison recording parameters can comprise at least one adjusted comparison reconstruction parameter and the adjusted training recording parameters can comprise at least one adjusted training reconstruction parameter.

Advantageously the adjusted comparison recording parameters, in particular similarly to the initial training recording parameters, can have at least one adjusted comparison reconstruction parameter, in particular a number of adjusted comparison reconstruction parameters. The at least one adjusted comparison reconstruction parameter can in particular have all features and characteristics that have been described in relation to the at least one initial training reconstruction parameter and vice versa.

In a further advantageous form of embodiment of the proposed method for provision of a trained function the adjustment of the at least one parameter of the trained function can be based on federated learning and/or a stochastic gradient method.

Federated learning can comprise local training, which is carried out separately on various client systems, for example in various hospitals. This enables a trained function with adjusted parameters to be provided for each local system in each case. Subsequently the local trained functions can be merged in a global model. Such training can take place in a number of rounds, wherein the global model can be distributed meanwhile to the local systems, in order to be further adjusted by local training. Advantageously a transmission of sensitive data, for example patient data, outside of a closed network, in particular of the local system, can be prevented, wherein the data can still be used as input data for local training of the trained function. The training dose profiles and the initial training recording parameters can advantageously be acquired and processed without regard to the respective training examination object.

As an alternative or in addition the adjustment of the at least one parameter of the trained function can be based on a stochastic gradient method. In this case a gradient of the cost function can be determined with regard to the recording parameters. The determination of the gradient can comprise a determination of partial derivatives of the cost function with regard to the recording parameters. In this case the gradient of the cost function with regard to the recording parameters can advantageously be embodied as a vector. During an iterative adjustment of the at least one parameter of the trained function at least one recording parameter can be iteratively adjusted. The adjustment of the at least one recording parameters can advantageously comprise an addition and/or multiplication of the previous, in particular initial, recording parameters and the, in particular scaled, gradients of the cost function with regard to the recording parameters. Through a scaling of the gradient of the cost function with regard to the recording parameters an adjustment of the minimization speed of the minimization of the cost value is advantageously made possible. Through the adjustment of the recording parameters based on the gradient of the cost function with regard to the recording parameters a reduction of the cost value of the cost function is advantageously made possible.

In a third aspect, an embodiment of the present invention relates to a provision unit, which is embodied for carrying out a proposed method for provision of adjusted recording parameters.

In this case the provision unit can comprise a processing unit, a memory unit and/or an interface. The provision unit can be embodied to carry out a proposed method for provision of adjusted recording parameters, in which the interface, the processing unit and/or the memory unit are embodied to carry out the corresponding method steps.

In particular the interface can be embodied for acquisition of the dose profiles for provision of the adjusted recording parameters. The processing unit and/or the memory unit can further be embodied for application of the trained function to the input data.

The advantages of the proposed provision unit essentially correspond to the advantages of the proposed method for provision of adjusted recording parameters. Features, advantages or alternate forms of embodiment mentioned here can likewise be transferred to other claimed subject matter and vice versa.

In a fourth aspect, an embodiment of the present invention relates to a medical x-ray device, comprising an x-ray source, a photon-counting x-ray detector and a proposed provision unit. In this case the x-ray source is embodied for sending out x-ray radiation. The x-ray detector further has a number of photon-counting detector elements, which are embodied to provide a dose value depending on a number of detected x-ray photons of incident x-ray radiation.

Advantageously the medical x-ray device can be embodied as a computed tomography system (CT system) and/or as a C-arm x-ray device and/or O-arm x-ray device.

The advantages of the proposed imaging device essentially correspond to the advantages of the proposed method for provision of adjusted recording parameters. Features, advantages or alternate forms of embodiment mentioned here can likewise also be transferred to the other claimed subject matter and vice versa.

In a fifth aspect, an embodiment of the present invention relates to a training unit, which is embodied for carrying out a proposed method for provision of a trained function.

In this case the training unit can advantageously comprise a training interface, a training memory unit and/or a training processing unit. The training unit can be embodied to carry out a method for provision of a trained function, in that the training interface, the training memory unit and/or the training processing unit are embodied to carry out the corresponding method steps.

In particular the training interface can be embodied for acquisition of the training dose profiles for provision of the trained function. The training processing unit and/or the training memory unit can further be embodied for carrying out the other method steps, in particular the first classification, the second classification, the provision of the adjusted comparison recording parameters, the application of the trained function to the input data and/or the adjustment of the at least one parameter of the trained function.

The advantages of the proposed training unit essentially correspond to the advantages of the proposed method for provision of a trained function. Features, advantages or alternate forms of embodiment mentioned here can likewise also be transferred to the other claimed subject matter and vice versa.

In a sixth aspect, an embodiment of the present invention relates to a non-transitory computer program product with a computer program, which is able to be loaded directly into a memory of a provision unit, with program sections for carrying out all steps of a proposed method for provision of adjusted recording parameters when the program sections are executed by the provision unit and/or which is able to be loaded directly into a training memory of a training unit, with program sections for carrying out all steps of a proposed method for provision of a trained function when the program sections are executed by the training unit.

Embodiments of the present invention can further relate to a computer program or non-transitory computer-readable memory medium, comprising a trained function, which has been provided by a proposed method or one of its aspects.

A largely software-based realization has the advantage that provision units and/or training units already previously used can be upgraded in a simple way by a software update in order to work in the inventive way. Such a computer program product, as well as the computer program can, where necessary, comprise additional elements such as for example documentation and/or additional components, as well as hardware components, such as for example hardware keys (dongles etc.) for use of the software.

BRIEF DESCRIPTION OF THE DRAWINGS

Exemplary embodiments of the present invention are shown in the drawings and will be described in greater detail below. The same reference characters are used for the same features in different figures.

In the figures

DETAILED DESCRIPTION

Figure 1:
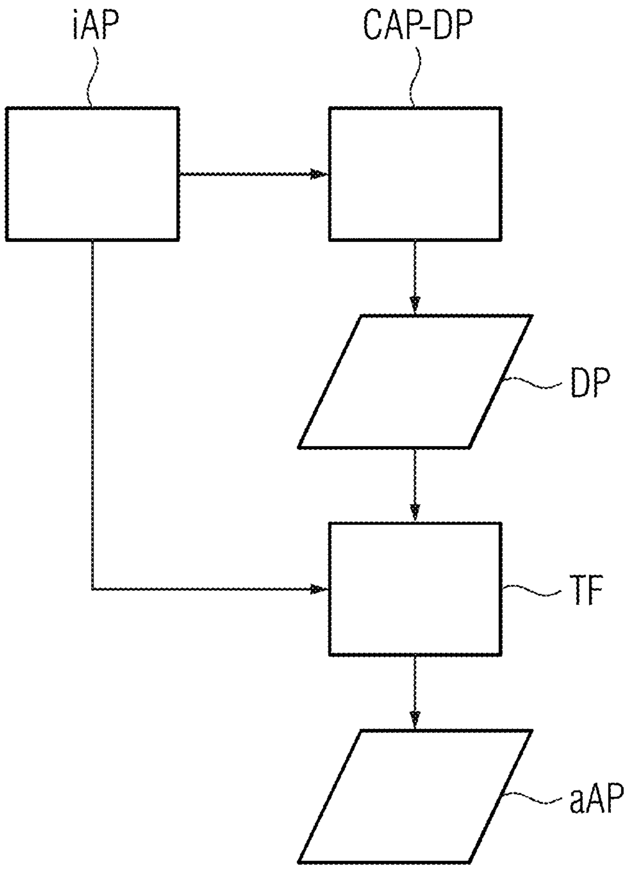
FIG. 1 shows a schematic diagram of a proposed computer-implemented method for provision of adjusted recording parameters.

FIG. 1 shows a schematic diagram of an advantageous form of embodiment of a proposed computer-implemented method for provision of adjusted recording parameters AP. In a first step spatially resolved dose profiles DP for an x-ray imaging scan of at least one examination object in each case can be recorded in accordance with initial recording parameters iAP via a photon-counting x-ray detector. In this case the x-ray detector can have a number of photon-counting detector elements, which each provide a dose value depending on a number of detected x-ray photons after an interaction between the x-ray radiation and the at least one examination object. The dose profiles DP can further be formed by the dose values of the detector elements of one of the number of x-ray imaging scans in each case. In a further step the adjusted recording parameters aAP are by applying a trained function TF to input data. In this case the input data can be based on the initial recording parameters and the dose profiles. The trained function TF can further be based on a dose-aware signal quality metric. Moreover the adjusted recording parameters aAP can be provided as output data to the trained function TF.

The input data of the trained function TF can be based in each case on a minimum value and/or maximum value and/or average value of the dose profiles DP. For example for each x-ray imaging scan one or more spatially resolved average values of the dose values, in particular average values of the detector signals in the x-ray detector can be established as count values, and subsequently be used as a reference value. The average values of the dose values can form in this case. The reference value represents a measure of how much x-ray radiation is still reaching the x-ray detector after the examination object. Per voxel a certain amount of x-ray quantas can be needed in order to achieve a sufficient SNR for diagnostic image quality. X-ray radiation exceeding this can represent an unnecessary x-ray dose load for the examination object.

The initial recording parameters iAP can further have information about a region to be imaged of the at least one examination object and/or a recording trajectory and/or a recording sequence and/or an operating parameter for operating the x-ray source and/or the x-ray detector. Moreover, the initial recording parameters iAP can comprise at least one initial reconstruction parameter for reconstruction of image data from the dose values. Furthermore the adjusted recording parameters aAP can comprise at least one adjusted reconstruction parameter.

Figure 2:
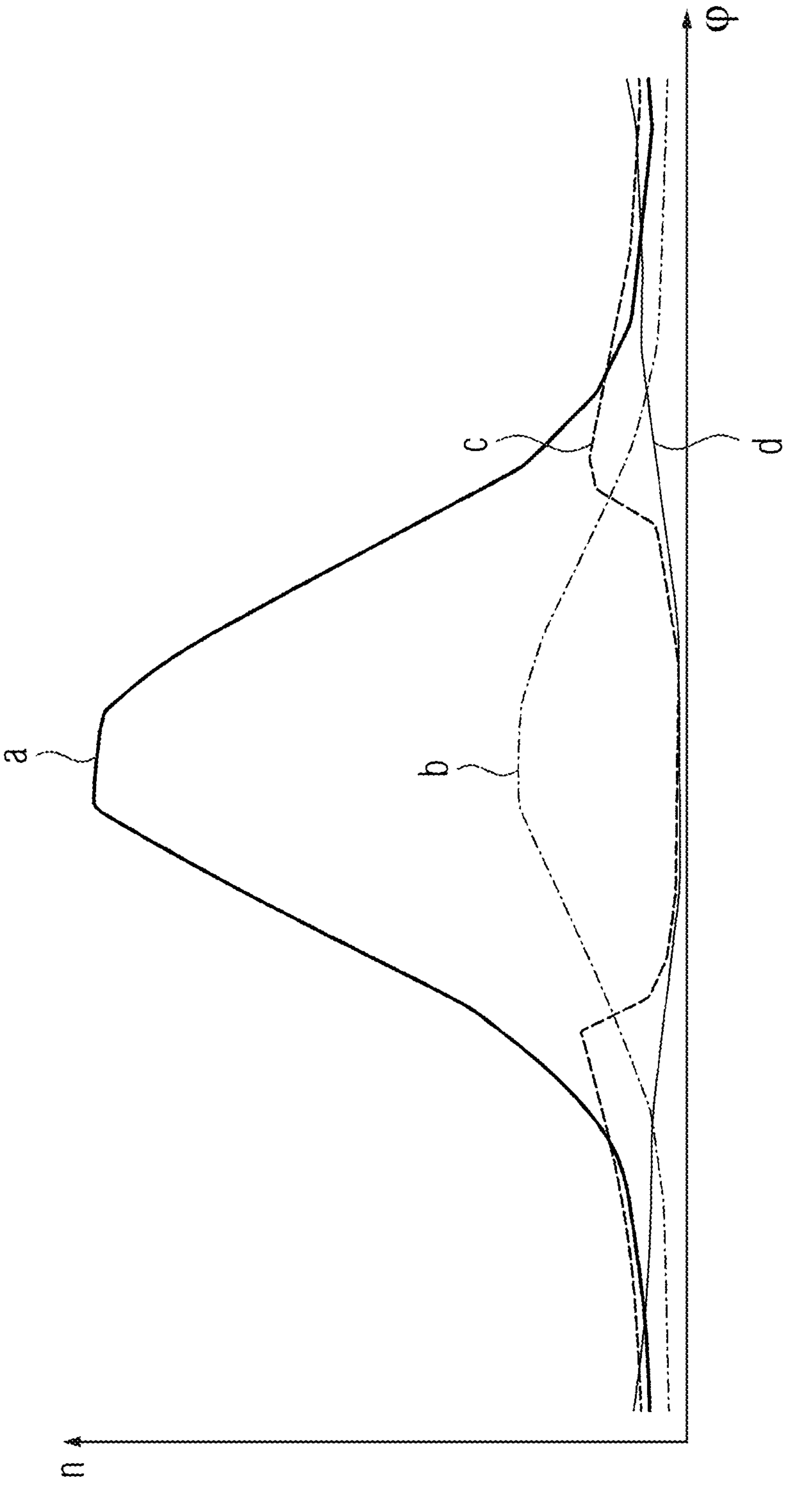
FIG. 2 shows a schematic diagram of examples of dose profiles.
Figure 3:
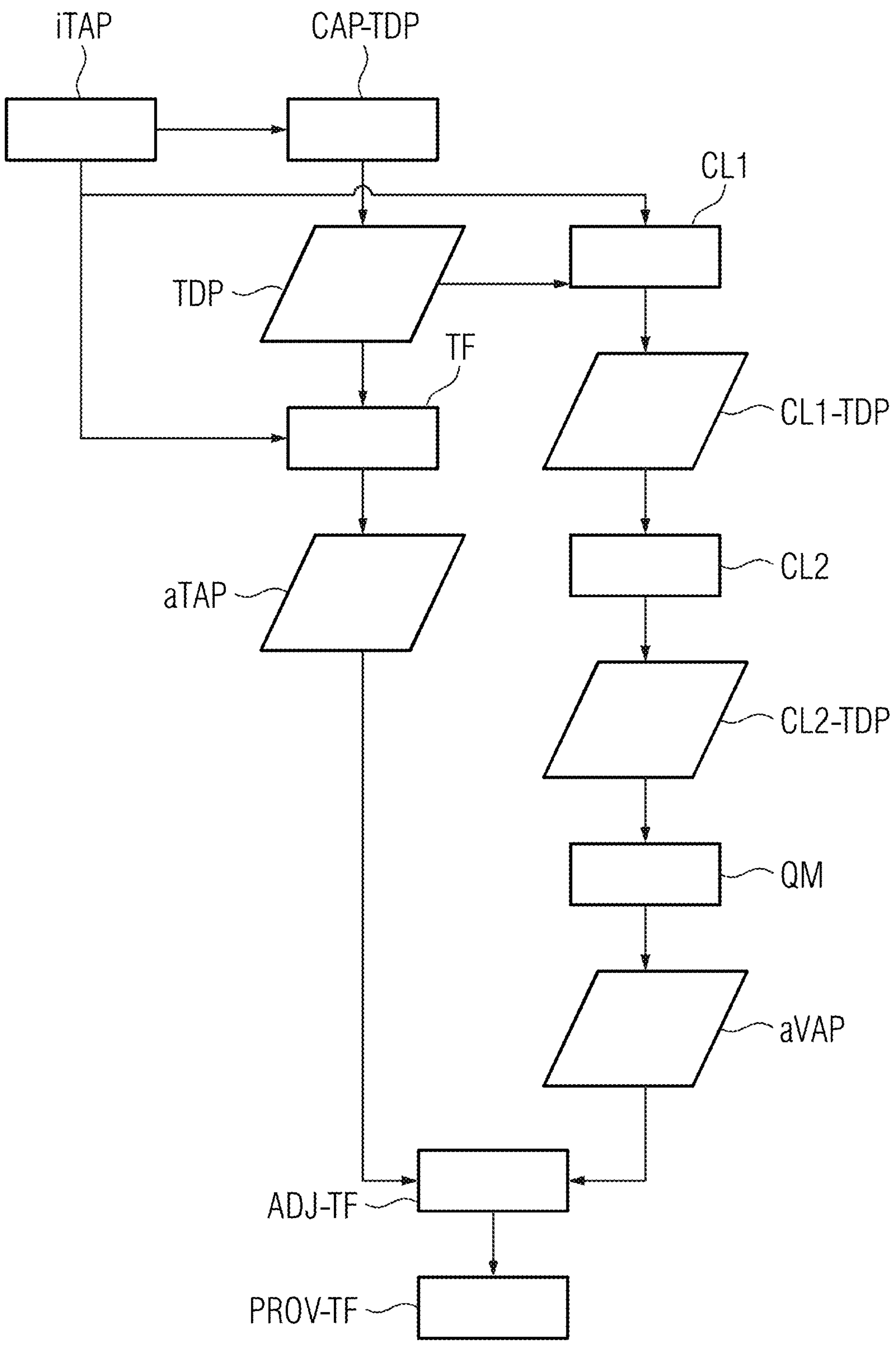
FIG. 3 shows a schematic diagram of a proposed computer-implemented method for provision of a trained function.

FIG. 2 shows a schematic diagram of examples of training dose profiles TDP, in particular count-value curves, such as can be acquired in a computer-implemented method for provision of a trained function (illustrated in FIG. 3). In this case the training dose values n are plotted against the projection angle φ for various measurement situations and/or training examination objects. In the first classification the training dose profiles TDP for example according to the region to be imaged of the at least one training examination object, in particular of a scan region, are classified. Depending on the scan region, for example a thorax, skull and/or extremities, classified training dose profiles CL1-TDP can be created by the training examination object. In this case the curve a shows a clear air recording, without a training examination object being arranged between x-ray source and x-ray detector, with a high x-ray dose. Curve b shows a further clear air recording, without a training examination object being arranged between x-ray source and x-ray detector, with a lower x-ray dose compared to the recording of curve a. Curve c shows a recording of an object, wherein a small training examination object, for example a head, is arranged between x-ray source and x-ray detector, with an medium x-ray dose. Curve d shows a further recording of an object, wherein a very large training examination object, for example a torso, is arranged between x-ray source and x-ray detector, with a high x-ray dose.

FIG. 3 shows a schematic diagram of an advantageous form of embodiment of a proposed computer-implemented method for provision of a trained function PROV-TF. In a first step spatially resolved training dose profiles TDP can be captured CAP-TDP for a real or simulated x-ray imaging scan of at least one training examination object in accordance with various initial training recording parameters iTAP via a photon-counting x-ray detector. The classified training dose profiles CL1-TDP can be standardized over time, in particular map photons per reading process. In this case the x-ray detector can have a number of photon-counting detector elements, which each provide a training dose value depending on a number of detected x-ray photons after an interaction between the x-ray radiation and the at least one training examination object. The training dose profiles TDP can further be formed by the training dose values of the detector elements of one of a number of x-ray imaging scans in each case. In a further step a first classification CL1 of the training dose profiles TDP can be undertaken based on the respective initial training recording parameters iTAP. In a further step a second classification CL2 of the classified training dose profiles CL1-TDP into conformant and deviating training dose profiles CL2-TDP can be undertaken by applying a dose-aware signal quality metric QM, which evaluates the signal quality while taking into account an overall dose in each case, to the training dose profiles CL1-TDP within a first class in each case. In a further step adjusted comparison recording parameters aVAP are based on the initial training recording parameters iTAP of the training dose profiles classified as conformant. After this, adjusted training recording parameters aTAP can be provided by applying the trained function TF to input data, wherein the input data is based on the initial training recording parameters iTAP and the training dose profiles TDP. After this, at least one parameter of the trained function TF can be adjusted ADJ-TF based on a comparison between the adjusted training recording parameters aTAP and the adjusted comparison recording parameters aVAP. The trained function TF can further be provided PROV-TF.

The input data of the trained function TF can be based on a minimum value and/or maximum value and/or average value of the training dose profiles TDP. The initial training recording parameters iTAP can further have information about a region to be imaged of the at least one examination object and/or a recording trajectory and/or a recording sequence and/or an operating parameter for operating the x-ray source and/or the x-ray detector. Moreover the initial training recording parameters iTAP can comprise at least one initial training reconstruction parameter for reconstruction of image data from the training dose values. The adjusted comparison recording parameters aVAP can further comprise at least one adjusted comparison reconstruction parameter and the adjusted training recording parameter aTAP at least one adjusted training reconstruction parameter. Advantageously the adjustment ADJ-TF of the at least one parameter of the trained function TF can be based on federated learning and/or a stochastic gradient method.

Figure 4:
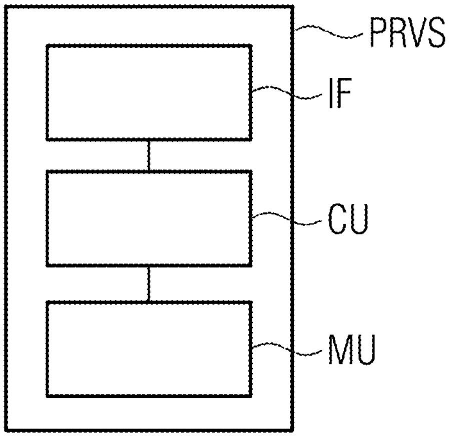
FIG. 4 shows a schematic diagram of a proposed provision unit.

FIG. 4 shows a schematic diagram of a proposed provision unit PRVS. In this case the provision unit PRVS can comprise a processing unit CU, a memory unit MU and/or an interface IF. The provision unit PRVS can be embodied to carry out a proposed method for provision of adjusted recording parameters, in which the interface IF, the processing unit CU and/or the memory unit MU are embodied to carry out the corresponding method steps.

Figure 5:
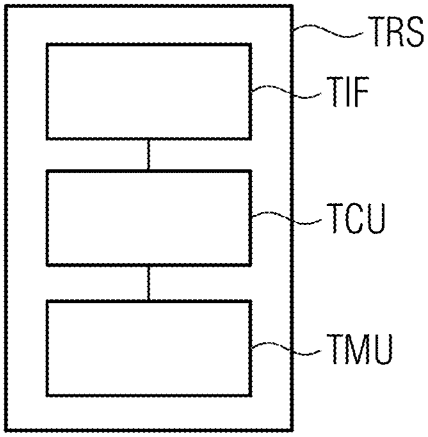
FIGS. 5 and 6 show schematic diagrams of advantageous forms of embodiment of proposed training units.

FIG. 5 shows a schematic diagram of an advantageous form of embodiment of a proposed training unit TRS. In this case the training unit TRS can advantageously comprise a training interface TIF, a training memory unit TMU and/or a training processing unit TCU. The training unit TRS can be embodied to carry out a method for provision of a trained function PROV-TF, in that the training interface TIF, the training memory unit TMU and/or the training processing unit TCU are embodied to carry out the corresponding method steps.

Figure 6:
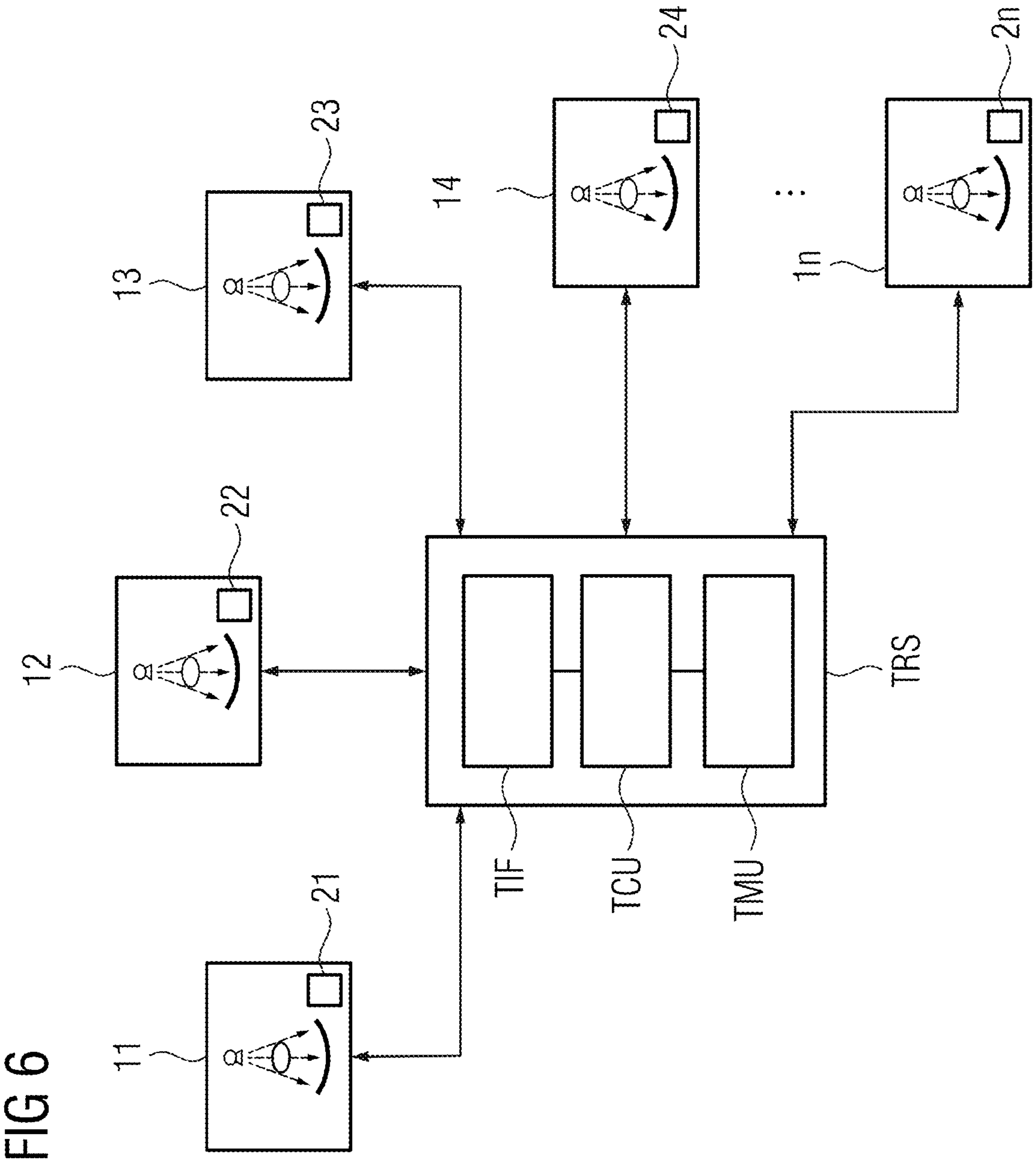

FIG. 6 shows a schematic diagram of a further advantageous form of embodiment of a proposed training unit TRS. In this case the adjustment ADJ-TF of the at least one parameter of the trained function TF can be based on federated learning. The federated learning can comprise local training, which is carried out separately on various local systems 11, 12, 13, 14 to 1*n*, for example in various hospitals. This enables a trained function 21, 22, 23, 24 to 2*n* to be provided with adjusted parameters for each local system 11, 12, 13, 14 to 1*n*. Subsequently the local trained functions 21, 22, 23, 24 to 2*n* can be merged in a global model. Such training can take place in a number of rounds, wherein the global model can meanwhile be distributed to the local systems 11, 12, 13, 14 to 1*n*, in order to be further adjusted by local training. Advantageously this enables a transmission of sensitive data, for example patient data, outside of a closed network, in particular the local system, to be prevented, wherein the data can still be used for local training of the trained function 21, 22, 23, 24 to 2*n* as input data.

Figure 7:
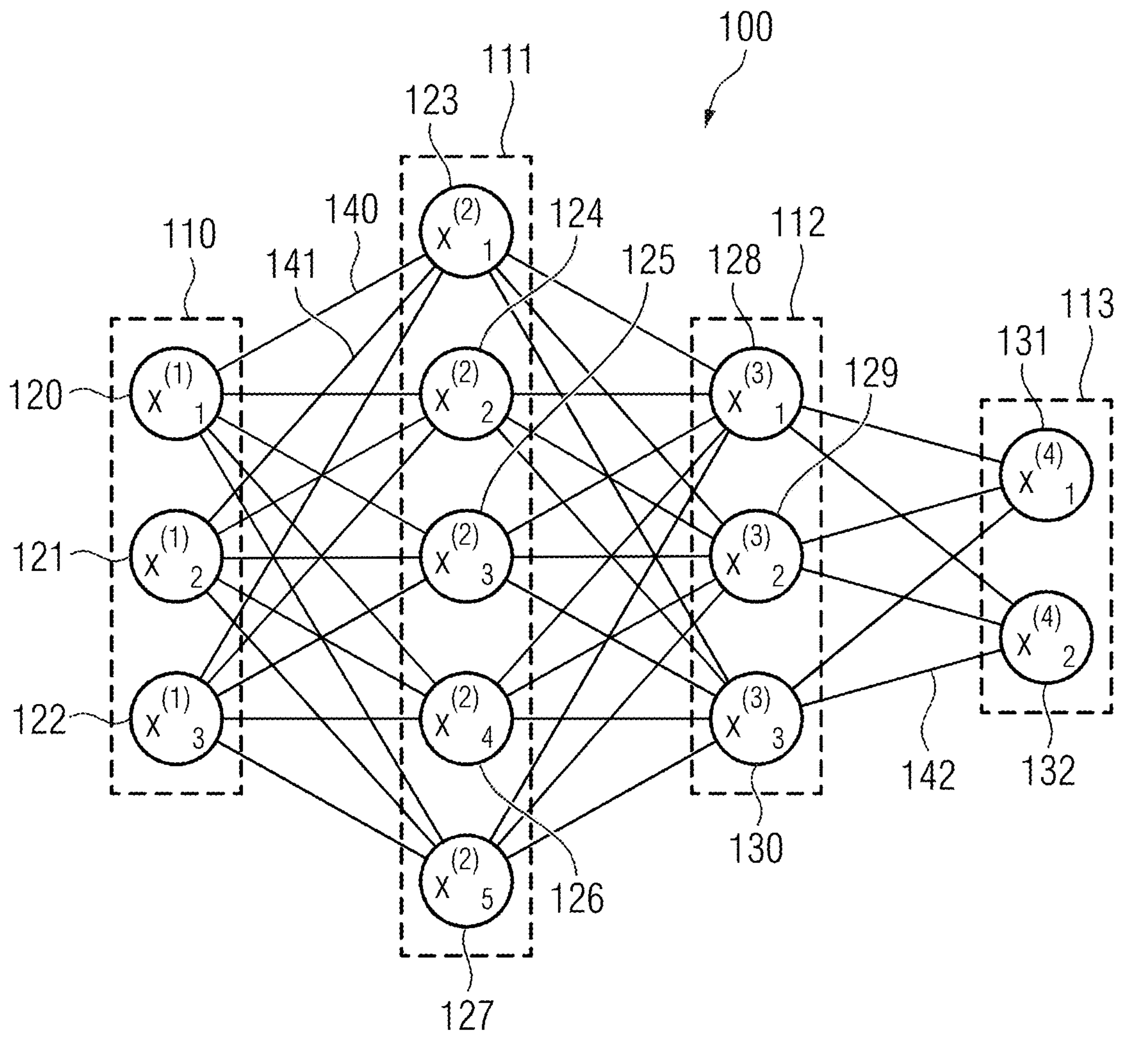
FIG. 7 shows a schematic diagram of an artificial neural network.

FIG. 7 shows a schematic diagram of an artificial neural network 100, as can be employed in a method in accordance with FIG. 2. The neural net can also be referred to as an artificial neural net, artificial neural network or neural network.

The neural net 100 comprises nodes 120, . . . , 132 and edges 140, . . . , 142, wherein each edge 140, . . . , 142 is a directed connection from a first node 120, . . . , 132 to a second node 120, . . . , 132. In general the first nodes 120, . . . , 129 and the second nodes 120, . . . , 132 are different nodes, it is also possible for the first nodes 120, . . . , 132 and the second nodes 120, . . . , 132 to be identical. An edge 140, . . . , 142 from a first node 120, . . . , 132 to a second node 120, . . . , 132 can also be referred to as an ingoing edge for the second node and as an outgoing edge for the first node 120, . . . , 132.

The neural net 100 responds to input values x(1)1, x(1)2, x(1)3 for a plurality of ingoing nodes 120, 121, 122 of the input layer 110. The input values x(1)1, x(1)2, x(1)3 are applied in order to create one or a plurality of outputs x(4)1, x(4)2. The node 120 is for example connected via an edge 140 to the node 123. The node 121 is for example connected via the edge 141 to the node 123.

The neural network 100 learns in this exemplary embodiment by adapting the weighting factors wi,j (weights) of the individual nodes based on training data. The weights wi,j are also referred to below as weight factors. Possible input values x(1)1, x(1)2, x(1)3 of the ingoing nodes 120, 121, 122 can for example be the training dose profiles TBD and the initial training recording parameters iTAP.

The neural network 100 weights the input values of the input layer 110 based on the learning process. The output values of the output layer 113 of the neural network 100 preferably correspond to the adjusted recording parameters or the adjusted training recording parameters. The output can however occur via a single or via a plurality of output nodes x(4)1, x(4)2 in the output layer 113.

In particular each node 120, . . . , 132 of the neural network 100 can be assigned a (real) number as a value. In this case x(n)i refers to the value of the ith node 120, . . . , 132 of the nth layer 110, . . . , 113. The values of the nodes 120, . . . , 122 of the input layer 110 are equivalent to the input values of the neural network 100. The values of the nodes 131, 132 of the output layer 113 are equivalent to the output values of the neural network. The artificial neural network 100 preferably comprises a number of hidden layers 111 and 112, which comprise a plurality of nodes x(2)1, x(2)2, x(2)3, x(2)4, x(2)5 and x(3)1, x(3)2, x(3)3. In this case a hidden layer 112 can use output values of another hidden layer 111 as input values. The nodes of a hidden layer 111 and 112 perform mathematical operations. For these each edge 140, . . . , 142 can have a weighting factor wi,j.

An output value of a node x(2)1, x(2)2, x(2)3, x(2)4, x(2)5 corresponds in this case to a non-linear function f of its input values x(1)1, x(1)2, x(1)3 and of the weighting factors wi,j. After the receipt of input values x(1)1, x(1)2, x(1)3 a node x(2)1, x(2)2, x(2)3 carries out a summation of a multiplication of each input value x(1)1, x(1)2, x(1)3 weighted with the weighting factor wi,j, as defined by the following function:

$$x_j^{(n+1)} = f\left(\sum_i x_i^{(n)} \cdot w_{i,j}^{(n)}\right).$$

The weighting factor wi,j can in particular be a real number, in particular lie in the interval of [−1;1] or [0;1]. The weighting factor $$w_{i,j}^{(m,n)}$$

designates the weight of the edge between the ith node of an mth layer 110, . . . , 113 and a jth node of the nth layer 110, . . . , 113. The weighting factor $$w_{i,j}^{(m,n)}$$

is an abbreviation for the weighting factor with $$w_{i,j}^{(n,n+1)}.$$

In particular an output value x(3)1, x(3)2, x(3)3 of a node x(2)1, x(2)2, x(2)3, x(2)4, x(2)5 is formed as a function f of a node activation, for example a sigmoidal function or a linear ramp function. The output values x(3)1, x(3)2, x(3)3 are transmitted to the output node or nodes 128, . . . , 130. An output value of the nodes x(4)1, x(4)2 is formed once again as a function f of a node activation. The output values x(4)1, x(4)2 are transmitted to the output node or nodes 131, 132.

The neural network 100 shown here is a feedforward neural network, in which all nodes 111 process the output values of a previous layer in the form of a weighted sum as input values. It goes without saying that other neural networks type can also be used in accordance with embodiments of the present invention, for example feedback networks, in which an input value of a node can at the same time also be its output value.

The neural network 100 is trained via a method of supervised learning to recognize patterns. A known method of operation is backpropagation, which can be applied for all exemplary embodiments of the present invention. During the training the neural network 100 is applied to input training data or values and must create corresponding, previously known outgoing training data or values. Iteratively mean square errors (MSE) between calculated and expected output values are calculated and individual weighting factors wi,j are adjusted until such time as the deviation between calculated and expected output values lies below a predetermined threshold value.

Figure 8:
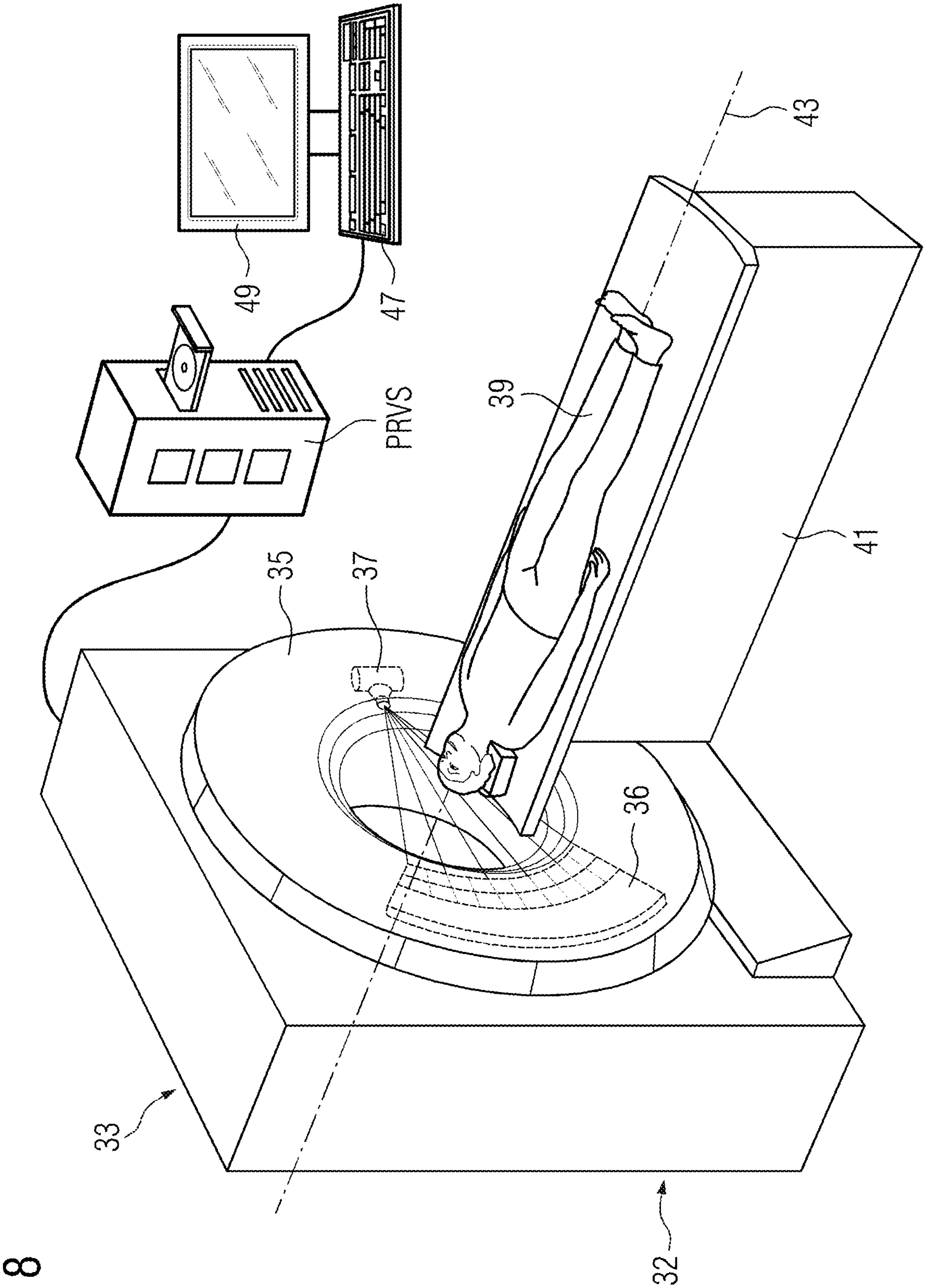
FIG. 8 shows a schematic diagram of a CT system.

FIG. 8 shows an example of a form of embodiment of a proposed medical X-ray device as a CT system 33, comprising an x-ray source 37, a photon-counting x-ray detector 36 and a proposed provision unit PRVS. In this example the x-ray source 37 and the x-ray detector 36 can be arranged positioned opposite one another. The x-ray source 37 can be embodied to illuminate the x-ray detector 36 with x-ray radiation in an incident x-ray direction. The CT-System 33 can moreover comprise a gantry 33 with a rotor 35. The x-ray source 37 and the x-ray detector 36 can be arranged in a defined arrangement on the rotor 35, in particular be integrated into or attached to the rotor 35. The rotor 35 can be supported to rotate about an axis of rotation 43. The examination object 39 can be supported on a patient couch 41 and be able to be moved along the axis of rotation 43 through the gantry 33. For control of the CT system 32 and for computation of slice images or volume images of the examination object 39, the provision unit PRVS can be used. An input facility 47, for example a keyboard, and an output apparatus 49, for example a screen and/or display, can be connected to the provision unit PRVS, in particular for signaling. The input facility 47 can advantageously be integrated into the output apparatus 49, for example in an, in particular resistive and/or capacitive, input display.

The schematic diagrams contained in the described figures do not depict scale or size relationships of any kind.

In conclusion it is pointed out once again that the method described in detail above, as well as the apparatus shown, merely represent exemplary embodiments, which can be modified by the person skilled in the art in a very wide variety of ways, without departing from the area of the present invention. Furthermore the use of the indefinite article "a" or "an" does not exclude the features concerned also being able to be present a number of times. Likewise the terms "unit" and "element" do not exclude the components involved consisting of a number of interacting sub-components that can, if necessary, also be spatially distributed.

The expression "based on" can be understood in the context of the present application in particular in the sense of the expression "using". In particular a formulation according to which a first feature is created (alternatively: established, determined etc.) based on a second feature, does not exclude that the first feature can be created (alternatively: established, determined etc.) based on a third feature.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being “directly” on, connected, engaged, interfaced, or coupled to another element, there are no intervening elements present. Other words used to describe the relationship between elements should be interpreted in a like fashion (e.g., “between,” versus “directly between,” “adjacent,” versus “directly adjacent,” etc.).

The terminology used herein is for the purpose of describing particular embodiments only and is not intended to be limiting of example embodiments. As used herein, the singular forms “a,” “an,” and “the,” are intended to include the plural forms as well, unless the context clearly indicates otherwise. As used herein, the terms “and/or” and “at least one of” include any and all combinations of one or more of the associated listed items. It will be further understood that the terms “comprises,” “comprising,” “includes,” and/or “including,” when used herein, specify the presence of stated features, integers, steps, operations, elements, and/or components, but do not preclude the presence or addition of one or more other features, integers, steps, operations, elements, components, and/or groups thereof. As used herein, the term “and/or” includes any and all combinations of one or more of the associated listed items. Expressions such as “at least one of,” when preceding a list of elements, modify the entire list of elements and do not modify the individual elements of the list. Also, the term “example” is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as “processing” or “computing” or “calculating” or “determining” of “displaying” or the like, refer to the action and processes of a computer system, or similar electronic computing device/hardware, that manipulates and transforms data represented as physical, electronic quantities within the computer system’s registers and memories into other data similarly represented as physical quantities within the computer system memories or registers or other such information storage, transmission or display devices.

In this application, including the definitions below, the term ‘module’ or the term ‘controller’ may be replaced with the term ‘circuit.’ The term ‘module’ may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A computer-implemented method for provision of adjusted recording parameters, the computer-implemented method comprising:

capturing spatially resolved dose profiles for an x-ray imaging scan of at least one examination object in accordance with initial recording parameters via a photon-counting x-ray detector, wherein the photon-counting x-ray detector has a plurality of photon-counting detector elements, each photon-counting detector element being configured to provide a dose value depending on a number of detected x-ray photons after interaction of x-ray radiation with the at least one examination object, and the spatially resolved dose profiles are formed by the dose values of the plurality of photon-counting detector elements of one or more x-ray imaging scans; and provisioning the adjusted recording parameters by applying a trained function to input data, wherein the input data is based on the initial recording parameters and the spatially resolved dose profiles, and the trained function is based on a dose-aware signal quality metric.

2. The computer-implemented method as claimed in claim 1, wherein the input data of the trained function is based on at least one of a minimum value, a maximum value or an average value of the spatially resolved dose profiles.

3. The computer-implemented method as claimed in claim 2, wherein the initial recording parameters have information about at least one of a region of the at least one examination object to be imaged, a recording trajectory, a recording sequence, an operating parameter for operation of an x-ray source, or the photon-counting x-ray detector.

4. The computer-implemented method as claimed in claim 3, wherein the initial recording parameters comprise at least one initial reconstruction parameter for reconstruction of image data from the dose values.

5. The computer-implemented method as claimed in claim 1, wherein the initial recording parameters have information about at least one of a region of the at least one examination object to be imaged, a recording trajectory, a recording sequence, an operating parameter for operation of an x-ray source, or the photon-counting x-ray detector.

6. The computer-implemented method as claimed in claim 1, wherein the initial recording parameters comprise at least one initial reconstruction parameter for reconstruction of image data from the dose values.

7. The computer-implemented method as claimed in claim 6, wherein the adjusted recording parameters comprise at least one adjusted reconstruction parameter.

8. A computer-implemented method for provision of a trained function, the computer-implemented method comprising:

capturing spatially resolved training dose profiles for a respective real or simulated x-ray imaging scan of at least one training examination object in accordance with initial training recording parameters via a photon-counting x-ray detector, wherein the photon-counting x-ray detector has a plurality of photon-counting detector elements, each photon-counting detector element providing a training dose value based on a number of detected x-ray photons after an interaction between x-ray radiation and the at least one training examination object, and the spatially resolved training dose profiles are formed by the training dose values of the plurality of photon-counting detector elements of one or more x-ray imaging scans;

first classifying the spatially resolved training dose profiles based on the initial training recording parameters;

second classifying the first classified, spatially resolved, training dose profiles into conformant and deviating training dose profiles by application of a dose-aware signal quality metric to the training dose profiles within a first class, the dose-aware signal quality metric indicative of a signal quality while taking into account a respective overall dose;

provisioning adjusted comparison recording parameters based on the initial training recording parameters of the spatially resolved training dose profiles classified as conformant;

provisioning adjusted training recording parameters by applying the trained function to input data, wherein the input data is based on the initial training recording parameters and the spatially resolved training dose profiles;

adjusting at least one parameter of the trained function based on a comparison of the adjusted training recording parameters with the adjusted comparison recording parameters; and provisioning the trained function.

9. The computer-implemented method as claimed in claim 8, wherein the input data of the trained function is based on at least one of a minimum value, a maximum value, or an average value of the spatially resolved training dose profiles.

10. The computer-implemented method as claimed in claim 9, wherein the initial training recording parameters have information about at least one of a region of the at least one training examination object to be imaged, a recording trajectory, a recording sequence, an operating parameter for operation of an x-ray source, or the photon-counting x-ray detector.

11. The computer-implemented method as claimed in claim 10, wherein the initial training recording parameters comprise at least one initial training reconstruction parameter for reconstruction of image data from the training dose values.

12. The computer-implemented method as claimed in claim 8, wherein the initial training recording parameters have information about at least one of a region of the at least one training examination object to be imaged, a recording trajectory, a recording sequence, an operating parameter for operation of an x-ray source, or the photon-counting x-ray detector.

13. The computer-implemented method as claimed in claim 8, wherein the initial training recording parameters comprise at least one initial training reconstruction parameter for reconstruction of image data from the training dose values.

14. The computer-implemented method as claimed in claim 13, wherein the adjusted comparison recording parameters include at least one adjusted comparison reconstruction parameter and the adjusted training recording parameters include at least one adjusted training reconstruction parameter.

15. The computer-implemented method as claimed in claim 8, wherein the adjusting of the at least one parameter of the trained function is based on at least one of a federated learning or a stochastic gradient method.

16. A provision unit configured to perform the computer-implemented method as claimed in claim 1.

17. A medical x-ray device, comprising:

an x-ray source configured to output x-ray radiation;

a photon-counting x-ray detector having a plurality of photon-counting detector elements, the plurality of photon-counting detector elements configured to provide dose values based on a number of detected x-ray photons of incident x-ray radiation; and the provision unit as claimed in claim 16.

18. A non-transitory computer-readable medium storing computer-executable instructions that, when executed by at least one processor at a provision unit, cause the provision unit to perform the computer-implemented method of claim 1.

19. A training unit configured to perform the computer-implemented method as claimed in claim 8.

20. A non-transitory computer-readable medium storing computer-executable instructions that, when executed by at least one processor at a training unit, cause the training unit to perform the computer-implemented method of claim 8.

* * * * *